March 16, 1948. H. C. SWIM Plant Pat. 792
ROSE PLANT
Filed Feb. 19, 1947
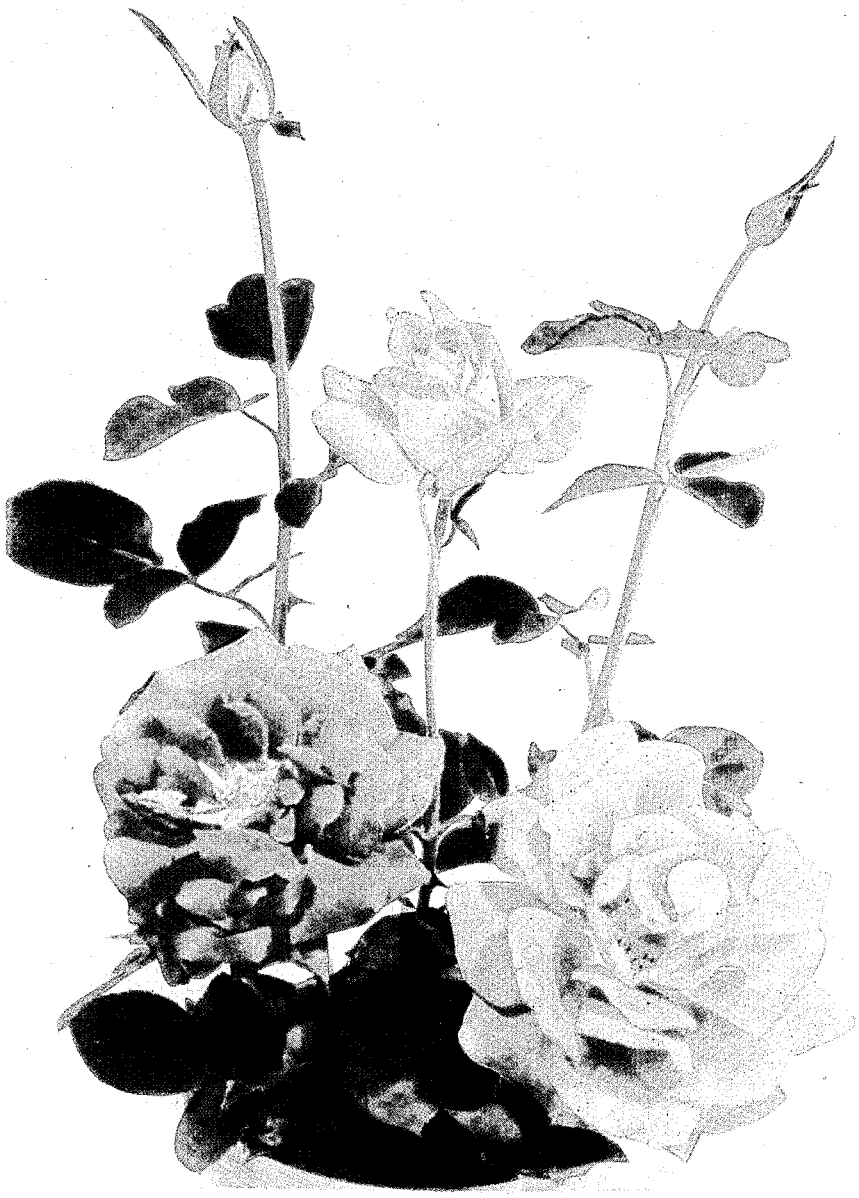
Inventor
H. C. Swim
By Robb & Robb
Attorneys Patented Mar. 16, 1948

Plant Pat. 792

UNITED STATES PATENT OFFICE

792

ROSE PLANT

Herbert C. Swim, Ontario, Calif., assignor to Armstrong Nurseries, Inc., Ontario, Calif., a corporation of California Application February 19, 1947, Serial No. 729,599

1 Claim. (Cl. 47—61)

The present invention relates to a new and distinct variety of hybrid tea rose plant which I have produced by crossing the variety "Contrast" with the variety "Charlotte Armstrong."

The breeding above referred to has resulted in a variety which is not only widely distinct from its parents, but also from any other hybrid tea of which I am aware, these dominant distinctions being listed as follows:

(1) The new variety is a very vigorous upright-growing plant, with moderate branching habit and foliage which shows a high degree of resistance to mildew and anthracnose.

(2) The foliage is flat, glossy, dark green in color, medium sized on growth produced in the spring season but increasing in size until it attains large proportions during the late summer and fall.

(3) The plant growth is characterized by the long, moderately heavy stems producing a fairly large number of medium to large thorns in the spring which, however, thereafter diminish in number until by fall the stems are relatively free of thorns.

(4) The flower combines a shape (hereinafter described) in both bud and open bloom with a wide contrast between the outside surface petal color and the inside surface petal color, this inside petal color being of extreme brilliance in the opening bud and newly opened flower.

It may also be desirable to compare this new variety with its parents, and, in this connection, it may be said that it is similar in many respects to its seed parent "Contrast," but differs therefrom in some very important respects: that is, (1) the foliage of the new rose is darker green in color, somewhat heavier, flatter, and attains a larger size; (2) the foliage is also highly resistant to mildew, whereas the foliage of "Contrast" is quite susceptible to mildew; (3) the new rose differs from its seed parent in that the open blooms have more petals and are more symmetrical in shape; and (4) the color of the inner surface of the petals of the new variety is very much deeper and more brilliant not only than found in "Contrast," but any other variety known to me, with the possible exception of the variety called "Ronsard" (Pl. Pat. #284). In no other way does this new variety resemble the last-named variety.

With respect to the pollen parent, this new variety's only resemblance lies in its resistance to mildew, and to a less pronounced degree, in the form of the open bloom. In all other respects these two varieties differ to a pronounced degree.

Asexual reproduction of this new variety shows the foregoing characteristics come true to form and are established.

In the drawing are shown specimens of the new variety, depicting as nearly as possible the various distinctions referred to above, the blooms being illustrated in their different stages from bud to full-open flower.

The following is a detailed description of the new variety, color terminology being in accordance with Robert F. Wilson's Horticultural Colour Chart with exceptions noted from Ridgway's Color Standards and Nomenclature:

Type: Hardiness untested; tall; bush; outdoor; seedling; for cut flowers and garden decoration.
Class: Hybrid tea.
Breeding: Seedling.
*Seed parent.*—"Contrast." (Unpatented.)
*Pollen parent.*—"Charlotte Armstrong" (Pl. Pat. #455).
Propagation: Holds its distinguishing characteristics through succeeding propagations by budding.

*Flower*

Locality where grown: Ontario, California.
Flowers borne: Usually singly, sometimes two to three to stem; in irregular cluster; on strong, long stems.
Quantity of bloom: Free; outdoors.
Continuity: Continuous during growing season.
Fragrance: Slight; tea.
Bud:
*Peduncle.*—Long; medium to heavy; erect; almost smooth; very few gland-tipped cilia and prickles. *Color*—near Rainette Green, Plate XXXI (Ridgeway).
*Before caylx breaks.*—*Size*—medium. *Form*—medium long; ovoid, with foliaceous appendages, few glad-tipped cilia on the surface of the bud; with slender, much cut foliaceous parts extending beyond the tip of the bud equal to ¼ or more of its length.
*As calyx breaks.*—At base of petal, near Chartreuse Green, Plate 663/1, page 90, gradually varying to Geranium Lake, Plate 20/2, page 20, where petal is exposed to sun. *Sepals*—inner surface with fine, woolly tomentum. When the margin of a sepal is not covered by the margin of an adjacent sepal it has tomentum and stipitate glands on both margins; but if margin is covered with adjacent sepals, margin has only woolly tomentum.

*As first petal opens.*—*Size*—medium. *Form*—medium long; ovoid. *Color*—outside: Base of petal near Canary Yellow, Plate 2/2, page 2, gradually becoming irregularly blotched and washed with Porcelain Rose, Plate 620, page 147, particularly at upper margin of petal; inside: near Turkey Red, Plate 721, page 94, gradually changing to Turkey Red, Plate 721/3, page 94, at apex of petal varied somewhat by a slight iridescence with a blotch of Lemon Yellow, Plate 4, page 4, at base of petal.

*Opening.*—Bud opens up well.

Bloom:

*Size.*—When fully open, medium; 3½ inches to 4 inches.

*Petalage.*—Double; from 24 to 30 petals, plus 2 to 5 petaloids; arranged regularly to irregularly.

*Form.*—Full at first; becoming open; petals remaining at first very loosely rolled outward; becoming later, at maturity, tightly rolled outward.

Petals: Medium thick; leathery; with inside velvety and outside shiny to satiny.

*Shape.*—Outside: obovate with apex flat usually with one notch; intermediate: obovate with apex rounded to flat; inside: obovate-cuneate with apex rounded.

*Color.*—Colors may be modified by being blotched, shaded or washed with other colors.

This description of a newly opened flower was made from a rose grown outdoors in the month of October, at Ontario, California:

*Color.*—*Outside petal*—outside surface: base of petal Canary Yellow, plate 2/2, page 2, gradually varying to Orange Buff, Plate 507/2, page 133, shaded with Camellia Rose, Plate 622/2, page 148, particularly at margin; inside surface: near Turkey Red, Plate 721, page 94, with Rose Madder, Plate 23, page 23, at margin of apex of petal varied somewhat by a slight iridescence with a blotch of Aureolin, Plate 3, page 3, at base of petal. *Intermediate petal*—outside surface: base of petal Canary Yellow, Plate 2/1, page 2, gradually changing to Orange Bluff, Plate 507/2, page 133, shaded with Camellia Rose, Plate 622/1, page 148, particularly at upper margin of petal; inside surface: near Turkey Red, Plate 721, page 94, shading to Turkey Red, Plate 721/2, page 94, at apex of petal varied somewhat by a slight iridescence and with a blotch of Aureolin, Plate 3, page 3, at base of petal. *Inner petal*—outside surface: base of petal Canary Yellow, Plate 2/1, page 2, gradually changing to near Amber Yellow, Plate 505, page 132, shaded and blotched with Camellia Rose, Plate 622, page 148, particularly at upper margin of petal; inside surface: near Turkey Red, Plate 721, page 94, varied somewhat by a slight iridescence with a blotch of Aureolin, Plate 3, page 3, at base of petal.

This description was made from a rose that was open for three days outdoors in the month of October, at Ontario, California:

*Color.*—*Outside petal*—outside surface: base of petal Mimosa Yellow, Plate 602/1, page 143, gradually shading to Amber Yellow, Plate 505/3, page 132, slightly washed at upper margin of petal with Camellia Rose, Plate 622/3, page 148; inside surface: near Rose Red, Plate 724, page 158, washed with Crimson, Plate 22/1, page 22, particularly at margin of petal, varied somewhat by a slight iridescence with a large blotch of Aureolin, Plate 3/1, page 3, at base of petal. *Inside petal*—outside surface: base of petal Canary Yellow, Plate 2/3, page 2, gradually shading to Empire Yellow, Plate 603/3, page 66, with upper margin of petal slightly washed with Neyron Rose, Plate 623/3, page 76; inside surface: Rose Red, Plate 724, page 158, shading to Turkey Red, Plate 721/2, page 94, varied somewhat by a slight iridescence and with a blotch of Aureolin, Plate 3/2, page 3, at base of petal.

*General color effect.*—Newly opened flower—near Turkey Red, Plate 721, page 94, varied somewhat by a slight iridescence. Three days open—Rose Red, Plate 724/2, page 158.

*Behavior.*—Drop off cleanly. Fading in early October from Turkey Red, Plate 721, page 94, to Rose Red, Plate 724/2, page 158.

*Flower longevity.*—On bush in garden, 3 to 4 days in October. Cut roses grown outdoors kept at living-room temperatures, 2 to 3 days in October.

*Reproductive organs*

Stamens: Average number; arranged regularly about pistils, a few mixed with petaloids.

Filaments: Medium length; 4 to 10 mm. *Color*—Empire Yellow, Plate 603, page 66. Most with anthers.

Anthers: Medium size; all open at once approximately. *Color*—near Indian Yellow, Plate 6/2, page 6, at upper side; under side, near Indian Yellow, Plate 6/3, page 6.

Pollen: Moderate. *Color*—near Majolica Yellow, Plate 09, page 102.

Pistils: Average number, approximately 30 in number.

Styles: Uneven; medium length, 3 to 9 mm.; medium caliper; loosely bunched. *Color*—near Uranium Green, Plate 63/3, page 63; at base gradually changing to near Signal Red, Plate 719/3, page 93, near stigma.

Stigma: Grayish white, somewhat translucent.

Hips: This variety very seldom sets seed under garden conditions.

Foliage:

*Leaves.*—Compound of 5 to 7 leaflets; normal; medium to large; leathery; glossy.

*Leaflets.*—Shape—obtuse with apex subacute; base obtuse; margin doubly serrate.

*Color.*—*Mature*—upper surface: near Cerro Green, Plate V (Ridgway); under surface: between Asphodel Green, Plate XLI (Ridgway) and Pois Green, Plate XLI (Ridgway). *Young*—upper surface: near Hellebore Green, Plate XVII (Ridway). Margin washed with Madder Brown, Plate XIII (Ridgway); under surface: Deep Grape Green, Plate XLI (Ridgway) washed with Vandye Red, Plate XIII (Ridgway).

*Rachis.*—Medium. Upper side—grooved with stipitate glands on edges; under surface—moderately prickly.

*Stipules.*—Medium length; medium width with medium length points, turning out at an angle of more than 45°, recurved toward the stem.

*Disease.*—Resistant to mildew.

Growth:

*Habit.*—Upright; moderately branched.

*Growth.*—Vigorous.

*Canes.*—Medium to heavy.

*Main stems.*—Near Grape Green, Plate XLI (Ridgway). *Large Prickles*—several; long; almost straight; with long narrow base. Color—near Rood's Brown, Plate XXVIII (Ridgway). *Small prickles*—very few. Color—near Rood's Brown, Plate XXVIII (Ridgway). *Hairs*—none.

*Branches.*—Near Deep Chrysolite Green, Plate XXXI (Ridgway). *Large prickles*—several; medium length; almost straight; with moderately narrow base. Color—Clay Color, Plate XXIX (Ridgway). *Small prickles*—few. Color—near Clay Color, Plate XXIX (Ridgway). *Hairs*—none.

*New shoots.*—Near Asphodel Green, Plate XLI (Ridgway) washed with Vandyke Red, Plate XIII (Ridgway) on side exposed to sun. *Large prickles*—several; medium length; almost straight; with moderately narrow base. Color—near Asphodel Green, Plate XLI (Ridgway) washed with Vandyke Red, Plate XIII (Ridgway). *Small prickles*—few. Color—near Asphodel Green, Plate XLI (Ridgway) washed with Vandyke Red, (Plate XIII (Ridgway). *Hairs*—none.

I claim:

A new and distinct variety of rose plant, characterized as to novelty by the vigorous upright-growing habit; the production of flat, glossy dark-green medium size foliage during spring growing with increase in size until attainment of large proportions during late summer and fall; high resistance to mildew and anthracnose; by its long moderately heavy stems having a fairly large number of medium to large thorns in the spring which diminish in late season until relative freedom of thorns is reached; by the shape of bud and open bloom combined with wide contrast between outer surface petal color and inner surface petal color and extreme brilliance of the latter in the opening bud and newly opening flower, substantially as shown and described.

HERBERT C. SWIM.